United States Patent [19]

Hutson, Jr.

[11] Patent Number: 4,579,998
[45] Date of Patent: Apr. 1, 1986

[54] HF ALKYLATION WITH PRODUCT RECYCLE EMPLOYING TWO REACTORS

[75] Inventor: Thomas Hutson, Jr., Bartlesville, Okla.

[73] Assignee: Phillips Petroleum Company, Bartlesville, Okla.

[21] Appl. No.: 587,761

[22] Filed: Mar. 9, 1984

[51] Int. Cl.⁴ ............................................. C07C 2/56
[52] U.S. Cl. ................................................ 585/716
[58] Field of Search .................................... 585/716

[56] References Cited

U.S. PATENT DOCUMENTS

| Re. 28,724 | 2/1976 | Sobel | 585/716 |
|---|---|---|---|
| 2,374,262 | 4/1945 | Anderson | 585/716 |
| 2,442,160 | 5/1948 | Baker | 585/716 |
| 3,211,803 | 10/1965 | Chapman | 585/716 |
| 3,544,651 | 12/1970 | Chapman | 260/683.45 |
| 3,830,865 | 8/1974 | Anderson | 260/671 R |
| 3,846,505 | 11/1974 | Anderson | 260/683.45 |
| 3,911,043 | 10/1975 | Anderson | 260/863.45 |
| 4,179,475 | 12/1979 | Makovec et al. | 585/714 |
| 4,220,806 | 9/1980 | Mikulicz et al. | 585/716 |
| 4,304,947 | 12/1981 | Hutson, Jr. | 585/716 |
| 4,383,977 | 5/1983 | Hutson, Jr. et al. | 422/235 |

Primary Examiner—William R. Dixon, Jr.
Assistant Examiner—Cynthia A. Prezlock
Attorney, Agent, or Firm—A. W. Umphlett

[57] ABSTRACT

A continuous method and apparatus for contact of olefin with paraffin in the presence of HF catalyst to produce alkylate in which about one half of the olefin feedstock is passed to each of two riser reactors with product effluent from both reactors entering a common settling vessel with return of settled HF catalyst proportioned between the two reactors and the paraffin feedstock provided as fresh or alkylate fractionator side stream recycle to one reactor and as reaction product recycle from the settler to the other reactor.

8 Claims, 1 Drawing Figure

HF ALKYLATION WITH PRODUCT RECYCLE EMPLOYING TWO REACTORS

BACKGROUND OF THE INVENTION

This invention relates to the catalytic alkylation of a isoparaffin with one or more olefins. In one of its aspects this invention relates to apparatus for carrying out alkylation. In another of its aspects, this invention relates to apparatus and process employing dual reactors with a single settling vessel. In a further aspect of the invention, it relates to the recycle of reactor product effluent from the settler as a portion of reactor feed stock.

The catalytic alkylation of an isoparaffin with one or more olefins to produce a branched chain paraffin is a commercially important process for producing high-octane gasoline. Conventional catalytic alkylation processes usually involve the reaction of an isoparaffin, such as isobutane, with olefin, such as propylene, or, optionally, both propylene and a butene, in the presence of a liquid alkylation catalyst, such as hydrogen fluoride, followed by the separation of the unreacted feed stock and product hydrocarbons from the catalyst in a settling zone and the purification of the product alkylate by fractionation. It has now been found that a general process improvement over standard production using a single reactor can be accomplished by using dual reactors discharging product effluent into a common settler and by recycling a portion of the reacted product effluent from the settler as feed stock to the reaction. The benefits of the dual reactor process include improved alkylate quality and the reduction of the feed volume to the alkylate fractionator. The reduction of feed volume to the alkylate fractionator is important because the fractionator is a principal consumer of utilities in an alkylation plant. The invention is, therefore, useful to effect economies in the fractionator of a new plant, to increase the capacity of an existing plant by installing the novel two-reactor system and/or to increase alkylate product quality.

It is therefore an object of this invention to provide a method and apparatus for improving the alkylate quality in the alkylation of isoparaffin and olefin in the presence of a catalyst as compared to the quality of alkylate produced in a similar operation using standard single reactor operation. It is another object of this invention to provide a method and apparatus for reducing the load on the alkylate fractionator in a catalytic alkylation process as compared to a standard single-reactor catalyzed alkylation process. It is also an object of this invention to provide method and apparatus for reducing the overall utility requirement in an alkylation plant. It is also an object of this invention to provide method and apparatus for improving the capacity of an existing alkylation plant.

Other aspects, objects, and the various advantages of this invention will become apparent upon reading this specification and the appended claims in conjunction with the drawings.

STATEMENT OF THE INVENTION

In accordance with this invention, a method is provided for continuously preparing alkylate by contacting olefin with paraffin in the presence of HF catalyst. According to this method about one-half of the total olefin feed stock for the process is contacted with fresh and recycled paraffin in the presence of HF in a first riser reactor with the reactants present in a ratio of paraffin to olefin of about 6:1 to about 100:1. Reactor product effluent from the first reactor is discharged into a settling vessel from which settled HF is discharged from the base and the reactor product effluent which contains alkylate, unreacted feed stock and HF is removed above the reactor effluent inlet to the settler. A portion of the reactor product effluent from the settler is recycled into contact with the remaining about one-half of the total olefin feed stock in the presence of HF catalyst in a second riser reactor in which the reactants are present in a ratio of paraffin to olefin of about 6:1 to about 100:1. The reactor product effluent from the second reactor is discharged into the settler. Settled HF is discharged from the base of the settler and proportioned between the first and second riser reactors. After removal of the portion of the reaction product effluent used as recycle feed stock to the second reactor the remainder of the reaction product effluent from the settler is recovered as system product.

In an embodiment of the invention apparatus is provided for continuously preparing alkylate by contacting olefin with isoparaffin in the presence of HF catalyst. This apparatus has as components: (a) a first riser reactor having controlled inlet for (1) olefin feed stock, and (2) isoparaffin feed stock with this first reactor connected to a inlet source of HF catalyst and equipped to discharge effluent into a settler vessel, (b) a settler vessel having means for reactor product effluent discharge there into and of sufficient dimensions to allow separation of HF catalyst and reactor product effluent with discharge of HF from the base of the settler and removal of reaction product effluent from a point above the reactor discharge inlet, (c) a second riser reactor having controlled inlet for (1) a feed stock of reaction product effluent removed from the settler, and (2) olefin feed stock with a second reactor connected to an inlet source of HF catalyst and equipped to discharge reaction product effluent into the settler vessel, (d) means connected into the first reactor and the second reactor for removing HF from the settler vessel, cooling the HF catalyst and passing the catalyst into the reactors, (e) means for removing a portion of the reaction product effluent from the settler of system product, and (f) means for controlling (1) flow of feed stock to the reactors and (2) flow of system product from the apparatus.

BRIEF DESCRIPTION OF THE DRAWING

The FIGURE is a simplified schematic flow diagram of the invention process showing the preferred form of the alkylation reaction and recovery apparatus.

DETAILED DESCRIPTION OF THE INVENTION

Figure 1:
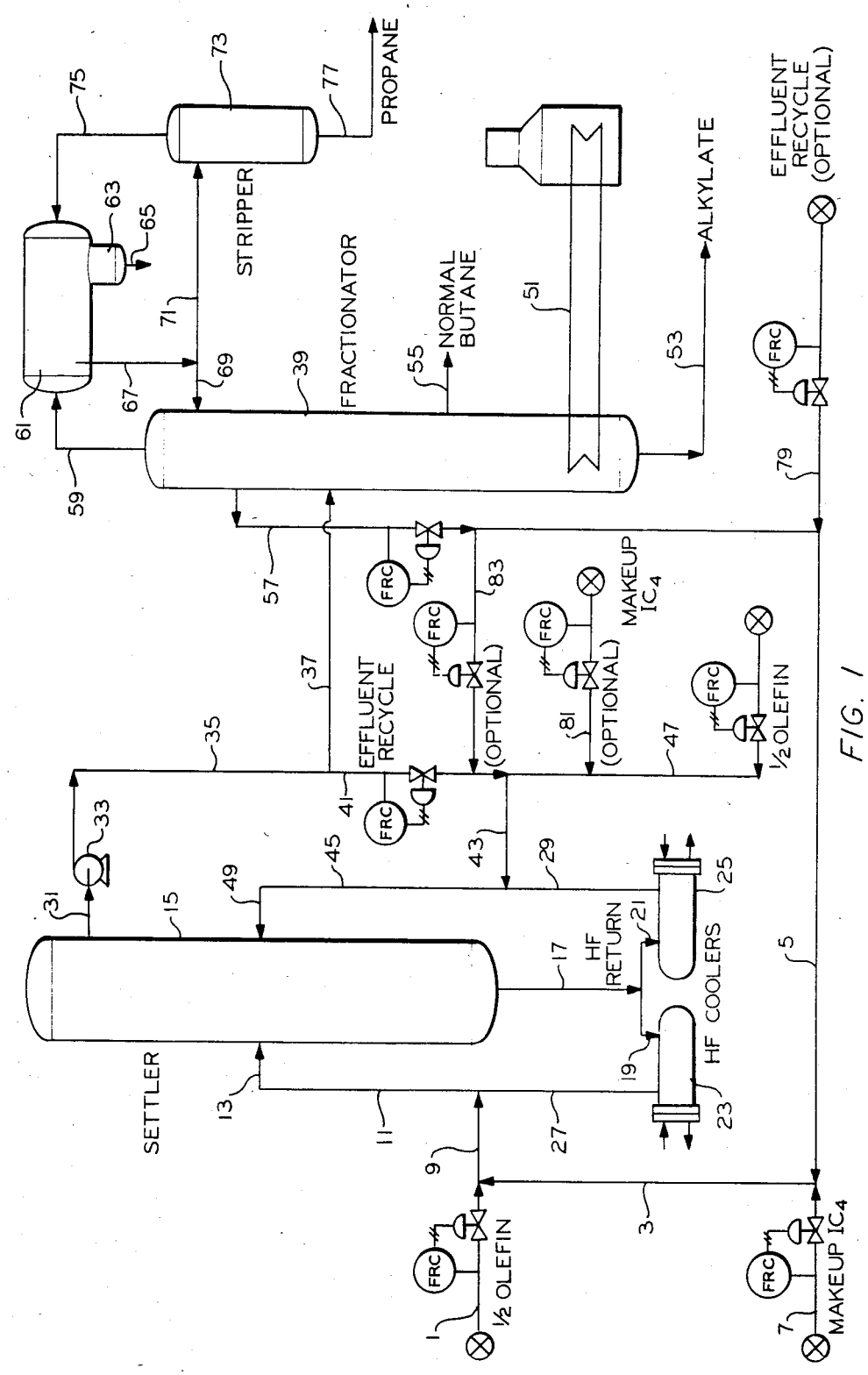

In the process of this invention, an isoparaffin is reacted with at least one olefin in the presence of a catalyst under conditions which maintain reactions and catalyst in the liquid phase. The isoparaffin can be any alkylatable isoparaffin such as isobutane or isopentane and the olefin can be a low molecular weight olefin such as propylene, a butene, an amylene, and like hydrocarbons, or a mixture of these. The alkylation catalyst is generally an acid-acting liquid such as sulfuric acid, hydrogen fluoride, phosphoric acid, a halo sulfonic acid or aluminum chloride. Hydrogen fluoride is a preferred catalyst because of its ability to be reused and because of the superior quality of the alkylate produced. When hydrogen fluoride catalyst is used it is generally in the form of 85 to 98 weight percent HF and 2 to 15 weight percent water, acid-soluble oils and hydrocarbons. The alkylates produced are branched paraffins, generally isomers of heptane, octane and like hydrocarbons. The process of this invention can be described more fully referring to the drawing, which illustrates an embodiment of the invention in which liquid isobutane is alkylated with a liquid mixture of propylene and butenes in liquid hydrogen fluoride catalyst.

A stream of olefin (1) at a temperature in the range of about ambient up to about 80° F. is mixed with a stream of isoparaffin (3) which can be a combination of recycle isoparaffin from the fractionation supplied by line (5) or makeup, fresh isoparaffin supplied by makeup line (7) and fed through line (9) into riser reactor (11) where it is mixed with HF catalyst under pressure sufficient to maintain reactants in liquid phase and at a reaction temperature generally in the range of about 70° to about 90° F. but which can range from about 40° to about 120° F. The ratio of isoparaffin to olefin will generally fall within a range of about 6:1 to about 100:1, preferably to about 10:1 to about 30:1.

The reactor product effluent which contains as major constituents alkylate product, unreacted reactants, and HF, is passed through line (13) into the settling vessel (15). In the settler (15) the HF is allowed to settle to the base of the vessel from which it is removed through line (17) and is proportioned through lines (19) (21) to pass through HF coolers (23) (25) and be returned through lines (27) (29) into the system reactors. Cooling liquid is passed in indirect heat exchange through the coolers to maintain the temperature in the reactors within the desired range.

Reactor product effluent from which most of the HF is separated is removed from the portion of the settler (15) above the reacted discharge inlets through line (31) and passed by means of pump (33) through line (35) and line (37) into the fractionator (39) or line (41) and (43) into the second riser reactor (45). The remaining one-half of the olefin feedstock is passed through line (47) and line (43) to be mixed with the reactor product effluent from the settler and HF catalyst from line (29) into the second riser reactor (45). Reactor effluent product from the second riser reactor is passed through line (49) into the settler. The second riser reactor is maintained within the pressure and temperature ranges set out for the first riser reactor and the ratio of isoparaffin to olefin is maintained within the range of about 6:1 to about 100:1, preferably about 10:1 to about 30:1.

Although in the preferred embodiment of the instant invention the first riser reactor mixes olefin feed stocks with the feed stock of isoparaffin which is obtained as fresh isoparaffin and isoparaffin recycled from the fractionation of alkylate product it is within the limitations of this invention also to use recycle of the reactor product effluent from the settler as part of the isoparaffin feed stock. Similarly, it is within the limitations of this invention optionally to use fresh makeup isoparaffin and/or recycle isoparaffin from the alkylate fractionation instead of or along with the preferred reactor product effluent from the settler as isoparaffin feed stock for the second riser reactor.

The fractionator (39) is affected by the process and apparatus of this invention in that the capacity of this piece of equipment can be reduced when the present invention is used. The fractionator has, therefore, been considered as at least an adjunct part of the present invention. Other than being affected in capacity the operation of the alkylate recovery system is conventional with the reactor product effluent from the settler entering fractionator (39) through line (37). In the fractionator the reactor product is subjected to a standard fractionation using indirect heat from kettle coil system (51) to separate an alkylate bottoms stream removed from the fractionator through line (53), a side draw of normal butane removed through line (55), a side draw of isobutane removed through line (57) to be returned as recycle to the reaction and an overhead stream principally of propane and HF removed through line (59) into an accumulator (61) in which there is a settling of the HF into settling leg (63) so that after collection it can be removed through line (65). A liquid stream of propane contaminated with HF is removed from the accumulator through line (67) and is used as reflux in the fractionator through line (69) or is passed through line (71) as feed stock in the stripping column (73). In the stripping column, HF contamination is removed overhead through line (75) for return to the accumulator and product grade propane is removed as a bottoms stream through line (77).

Control of the various feedstreams to the riser reactors can be accomplished by using a flow recorder controller to control flow through a motor valve operated in response to the flow sensed upstream of the control valve, which is standard procedure. For control of all the variations of feedstock contemplated in this invention flow recorder controllers would be necessary in lines 1, 7, 41, 47, 57, 79, 81 and 83.

The following are set out as examples for comparison for the process of the present invention with the standard process using a single reactor operation. The Examples should be taken as illustrative and not as restrictive.

EXAMPLE I

Set out below in Table I are stream flows for a two-reactor operation using a common settler as described in the disclosure above.

TABLE I

| Steam flows for two-reactor operation using a common settler as shown in FIG.: | |
|---|---|
| | Flow Rates, Bbl/Hour |
| Olefin feed to first reactor (1) | 5.0 |
| 45 vol % propylene | |
| 55 vol % butenes | |
| Olefin feed to second reactor (47) | 5.0 |
| 45 vol % propylene | |
| 55 vol % butenes | |
| Recycle isobutane from fractionator (5) | 76.5 |
| 91.5 vol % isobutane | |
| Effluent recycle to second reactor (43) | 146.6 |
| 68.2 vol % isobutane | |
| Fresh isobutane (7) | 13.7 |
| 91.5 vol % isobutane | |
| Alkylate product (53) | 18.0 |
| 94.0 Research Octane No., 0 CC TEL | |
| Feed to alkylate fractionator (57) | 102.6 |
| Process Conditions: | |
| Reactor temperature | 80 F. |
| Reactor pressure - to maintain liquid phase | |
| HF catalyst/total hydrocarbon ratio | 4.0:1 |
| (each reactor) | |
| HF Catalyst Composition, wt. % | |
| HF | 90.6 |
| $H_2O$ | 3.7 |
| Acid soluble oils | 0.2 |
| Hydrocarbons | 5.5 |
| Isobutane/olefin volume | 16.5:1 |

TABLE I-continued

Steam flows for two-reactor operation using a common settler as shown in FIG.:

| | Flow Rates, Bbl/Hour |
|---|---|
| ratio (1st reactor) | |
| Isobutane/olefin volume ratio (2nd reactor) | 20.0:1 |

EXAMPLE II

In Table II that follows are set out stream flows for single reactor operation using the same olefin feed, isobutane and HF compositions as set out in Example I above and using the same process conditions as set out above except that the isobutane/olefin volume ratio to the reactor is 14.0:1.

TABLE II

Stream flows for single reactor operation using the same olefin feed, isobutane and HF compositions as Example I and same process conditions except isobutane/olefin volume ratio to reactor is only 14.0:1.

| | Flow Rates Bbl/Hr |
|---|---|
| Olefin feed to reactor | 10.0 |
| 45 vol % propylene | |
| 55 vol % butenes | |
| Recycle isobutane from fractionator | 139.3 |
| 91.5 vol % isobutane | |
| Fresh isobutane | 13.7 |
| 91.5 vol % isobutane | |
| Alkylate product | 18.0 |
| 92.7 Research Octane No., 0 CC TEL | |
| Feed to alkylate fractionator | 158.5 |

Comparison of the two examples illustrates the two primary benefits of the invention: (1) improved alkylate quality and (2) reduced feed volume to the alkylate fractionator. Inventive Example I yields alkylate with 94.0 RON without the addition of tetraethyl lead (note in both Examples the 0 CC TEL describing the alkylate product) while the conventional reactor in Example II yields only 92.7 RON alkylate. Although the isobutane/olefin volume ratio is somewhat lower in the conventional reactor (14.0:1 vs 16.5:1 and 20:1 in the two-reactor operation), the volume of hydrocarbon to be fractionated for the conventional reactor is 158.5 bbl/hr while for the present invention it is 102.6 bbl/hr with the single reactor volume being about 54% greater in the present invention. This difference means that the conventional operation tends to require a larger fractionator which consumes greater energy for reboilingL—an increase of energy almost in proportion to the difference in the fractionator feed volumes. Since the fractionator is a principal consumer of utilities in an alkylation plant the invention can be used to effect economies in the fractionator of a new plant, to increase the capacity of an existing plant (by installation of the novel two-reactor system) and/or increase alkylate product quality (octane number).

I claim:

1. A method for continuously preparing alkylate by contacting olefin with paraffin in the presence of HF catalyst comprising:
   (a) contacting about one-half of the total olefin feed stock with fresh and recycle paraffin in the presence of HF catalyst in a first riser reactor to produce a first reactor product effluent, the reactants present in a ratio of paraffin to olefin of about 6:1 to about 100:1;
   (b) discharging said first reactor product effluent into a settler wherein settled HF catalyst is discharged from the base and reactor product effluent comprising alkylate, unreacted feed stock and HF catalyst is removed above the reactor effluent inlet to the settler;
   (c) recycling a portion of the reactor product effluent from the settler into contact with the remaining about one-half of the total olefin feed stock in the presence of HF catalyst in a second riser reactor to produce a second reactor product effluent, the reactants present in a ratio of paraffin to olefin of about 6:1 to about 100:1;
   (d) discharging said second reactor product effluent into said settler;
   (e) discharging settled HF catalyst from the settler base;
   (f) proportioning said HF catalyst between said first and said second riser reactor; and
   (g) recovering as system product from the settler the portion of said reaction product effluent remaining after removal of recycle.

2. A method of claim 1 wherein said system product is further treated by fractionation to provide a side stream of unreacted isoparaffin feed stock, a bottoms product of alkylate and an overhead comprising HF.

3. A method of claim 2 wherein said side stream of paraffin is recycled as feed stock to a reactor.

4. A method of claim 1 wherein paraffin is isobutane and olefin is a mixture of 45 volume % propylene and 55 volume % butenes.

5. A method of claim 2 wherein paraffin is isobutane and olefin is a mixture of 45% volume % propylene and 55 volume % butenes.

6. A method of claim 3 wherein paraffin is isobutane and olefin is a mixture of 45% volume % propylene and 55 volume % butenes.

7. A method of claim 5 wherein said overhead comprising HF is subjected to a stripping operation to produce a bottoms propane product stream.

8. A method of claim 1 wherein a controlled amount reactor product effluent is fed to the second riser reactor.

* * * * *